United States Patent
Grubac et al.

(10) Patent No.: US 10,130,821 B2
(45) Date of Patent: Nov. 20, 2018

(54) INTERVENTIONAL MEDICAL SYSTEMS AND ASSOCIATED TETHERING ASSEMBLIES AND METHODS

(71) Applicant: Medtronic, Inc., Minneapolis, MN (US)

(72) Inventors: Vladimir Grubac, Brooklyn Park, MN (US); Thomas A Anderson, New Hope, MN (US)

(73) Assignee: Medtronic, Inc., Minneapolis, MN (US)

( * ) Notice: Subject to any disclaimer, the term of this patent is extended or adjusted under 35 U.S.C. 154(b) by 608 days.

(21) Appl. No.: 14/696,009

(22) Filed: Apr. 24, 2015

(65) Prior Publication Data

US 2016/0310747 A1    Oct. 27, 2016

(51) Int. Cl.
| | | |
|---|---|---|
| A61B 17/34 | (2006.01) | |
| A61N 1/375 | (2006.01) | |
| A61N 1/372 | (2006.01) | |
| A61N 1/362 | (2006.01) | |
| A61B 17/22 | (2006.01) | |
| A61N 1/05 | (2006.01) | |
| A61B 17/00 | (2006.01) | |

(52) U.S. Cl.
CPC .......... *A61N 1/375* (2013.01); *A61B 17/3468* (2013.01); *A61N 1/362* (2013.01); *A61N 1/372* (2013.01); *A61N 1/37205* (2013.01); *A61B 17/22031* (2013.01); *A61B 2017/00292* (2013.01); *A61B 2017/00473* (2013.01); *A61N 1/0587* (2013.01); *A61N 1/3756* (2013.01); *A61N 2001/0578* (2013.01)

(58) Field of Classification Search
CPC .......... A61B 17/22031; A61B 17/3468; A61N 2001/0578
See application file for complete search history.

(56) References Cited

U.S. PATENT DOCUMENTS

| | | |
|---|---|---|
| 6,913,614 B2 | 7/2005 | Marino et al. |
| 7,011,671 B2 | 3/2006 | Welch |

(Continued)

OTHER PUBLICATIONS (PCT/US2016/028284) PCT Notification of Transmittal of the International Search Report and the Written Opinion of the International Searching Authority, dated Jul. 12, 2016, 12 pages.

(Continued)

*Primary Examiner* — Diane Yabut (57) ABSTRACT

An assembly for tethering a medical device to a delivery catheter includes a tether, a collet, and a spring-biased holding element that is coupled to a distal end of the tether and that extends around the collet, being moveable between first and second positions. At the first position, corresponding to the spring bias thereof, the holding element prevents fingers of the collet, which are configured to grip a proximal end of the device, from opening; at the second position, the collet fingers are allowed and/or caused to open. The assembly is coupled to a tubular member of the catheter, and, when the tethering assembly abuts a distal end of the catheter tubular member, a pull force applied to a proximal end the tether, which extends out from a proximal opening of the catheter, moves the holding element from the first position to the second position.

18 Claims, 9 Drawing Sheets

(56) References Cited

U.S. PATENT DOCUMENTS

| | | | |
|---|---|---|---|
| 8,615,310 B2 | 12/2013 | Khairkhahan et al. | |
| 8,958,892 B2 | 2/2015 | Khairkhahan et al. | |
| 2004/0059348 A1* | 3/2004 | Geske | A61B 17/22031 606/129 |
| 2005/0004644 A1* | 1/2005 | Kelsch | A61B 17/8888 607/131 |
| 2008/0071339 A1 | 3/2008 | Stalker et al. | |
| 2008/0283066 A1 | 11/2008 | Delgado et al. | |
| 2010/0268201 A1 | 10/2010 | Tieu et al. | |
| 2011/0270339 A1 | 11/2011 | Murray, III et al. | |
| 2012/0172690 A1 | 7/2012 | Anderson et al. | |
| 2013/0253345 A1 | 9/2013 | Griswold et al. | |
| 2013/0253347 A1 | 9/2013 | Griswold et al. | |
| 2014/0074114 A1 | 3/2014 | Khairkhahan et al. | |
| 2014/0142621 A1 | 5/2014 | Masters et al. | |
| 2015/0051610 A1 | 2/2015 | Schmidt et al. | |
| 2015/0051611 A1 | 2/2015 | Schmidt et al. | |
| 2015/0051682 A1 | 2/2015 | Schmidt et al. | |
| 2015/0094668 A1 | 4/2015 | Wood et al. | |
| 2015/0144358 A1* | 5/2015 | Mejia | E21B 23/006 166/382 |

OTHER PUBLICATIONS

Ronan Wood, et al., Interventional Medical Systems and Associated Tethering Assemblies and Methods, U.S. Appl. No. 62/132,662, filed Mar. 13, 2015, 20pp.

Ronan Wood, Catheters for Deploying Implantable Medical Devices, and Associated Tethering Assemblies and Methods, U.S. Appl. No. 14/630,832, filed Feb. 25, 2015, 19pp.

\* cited by examiner

INTERVENTIONAL MEDICAL SYSTEMS AND ASSOCIATED TETHERING ASSEMBLIES AND METHODS

FIELD OF THE DISCLOSURE

The present disclosure pertains to interventional medical systems, and more particularly to associated tethering assemblies and methods.

BACKGROUND

Figure 1:
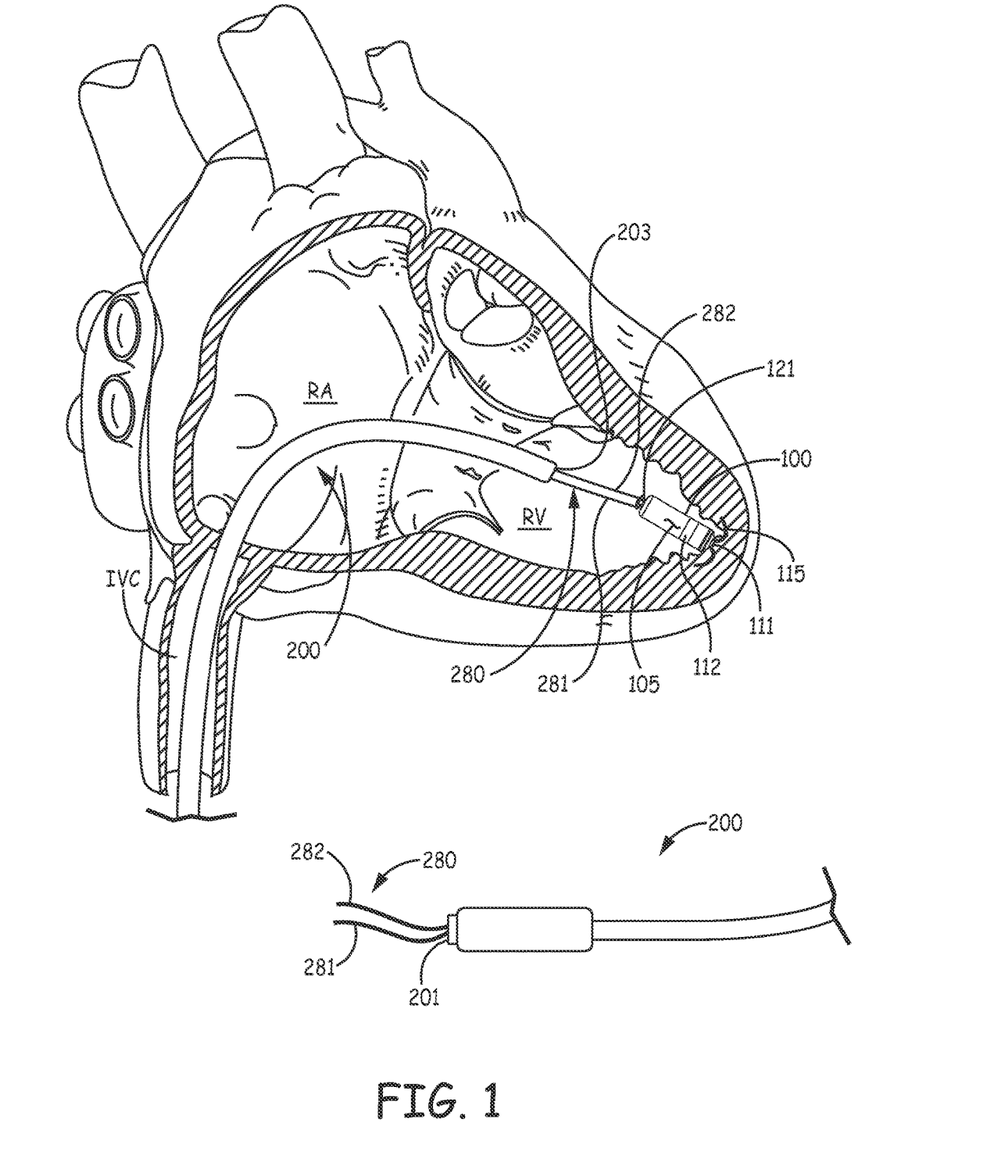
FIG. 1 is a schematic showing an exemplary implant of a relatively compact medical device, via an exemplary delivery catheter.

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MRI compatibility issues, which are sometimes associated with elongate lead wires and well known to those skilled in the art, have motivated the development of implantable cardiac pacing devices that are wholly contained within a relatively compact package for implant in close proximity to the pacing site, for example, within the right ventricle RV of the heart. With reference to FIG. 1, such a device 100 is illustrated, wherein an hermetically sealed housing 105, preferably formed from a biocompatible and biostable metal such as titanium, contains an electronic controller and associated power source (not shown), to which at least one electrode 111 is coupled, for example, by a hermetic feedthrough assembly (not shown) like those known to those skilled in the. Housing 105 may be overlaid with an insulative layer, for example, medical grade polyurethane, parylene, or silicone, and a portion of the insulation layer may be removed to form another electrode 112, for example, which provides bipolar pacing and sensing in conjunction with electrode 111.

FIG. 1 shows device 100 having been deployed by an operator out from a distal opening 203 of a delivery catheter 200, which the operator has maneuvered up through the inferior vena cava IVC and across the right atrium RA into the right ventricle RV. The deployed device 100 is shown fixed at an implant site by a fixation member 115 thereof, but still secured to catheter 200 by a tether 280 that extends out from distal opening 203 of catheter 200.

Securing device 100 to catheter 200 with tether 280 is typically accomplished by looping tether 280 through an attachment feature 121 of device 100 and threading first and second lengths 281, 282 of tether 280 through one or more lumens of catheter 200 such that opposing ends thereof protrude out from a proximal opening 201 of catheter 200. After deploying device 100, the operator can grasp the ends of lengths 281, 282 and tug on tether 280, for example, to test the fixation of device 100 at the implant site, and/or to apply a greater force to tether 280 to remove device 100 from the implant site for repositioning at a more suitable site, if necessary. If satisfied with the implant of device 100, the operator can un-tether device 100 from catheter 200 by releasing, for example, the end of tether length 281, and then pulling on the end of the other tether length 282, thereby withdrawing an entirety of length 282 proximally through delivery catheter 200 so that the other length 281 is pulled distally and through device tether attachment feature 121, out from engagement therewith.

SUMMARY

The present disclosure pertains to improved apparatus and methods related to the tethering of implantable medical devices in the context of deploying the devices at an implant site via a delivery catheter. According to some embodiments, an interventional medical system includes an implantable medical device and a delivery catheter for deploying the device at an implant site, wherein the device is tethered to the catheter by a tethering assembly of the catheter, which includes a tether, a collet, and a spring-biased holding element that is coupled to a distal end of the tether and that extends around the collet, being moveable between a first position, corresponding to the spring bias thereof, and a second position. At the first position, the holding element prevents an opening of fingers that form a distal portion of the collet, and which are configured to grip a proximal end of the device therein; and at the second position, the holding element allows and/or causes the fingers of the collet to open, so that the proximal end of the device can be inserted into the collet, or released from the grip of the collet. The tethering assembly is coupled to an elongate tubular member of the catheter, for example, by inserting the tether through a lumen of the tubular member so that a proximal end of the tether extends out from a proximal opening of the lumen at a proximal end of the catheter. And, according to some methods, a pull force applied to the proximal end of the tether, when the tethering assembly abuts a distal end of the catheter tubular member, moves the holding element from the first, spring-biased position, to the second position.

According to some embodiments the spring-biased holding element of the catheter tethering assembly includes a collar and a spring member, the tether being coupled to the collar, the collar extending around the collet and between the fingers thereof, and the spring member being mounted within an interior portion of the collet. According to some alternate embodiments, the spring-biased holding element of the catheter tethering assembly includes an elastic ring and a plate, to which the tether is coupled, wherein the elastic ring extends around the collet, and includes a distal collar, and a proximal base, which may be configured to fit together with the distal end of the catheter tubular member, and wherein the plate extends within an interior portion of the collet and includes a plurality of arms spaced apart from one another around a perimeter of the plate, each arm extending between adjacent fingers of the collet, and each arm being coupled to the distal collar of the elastic ring.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 2A:
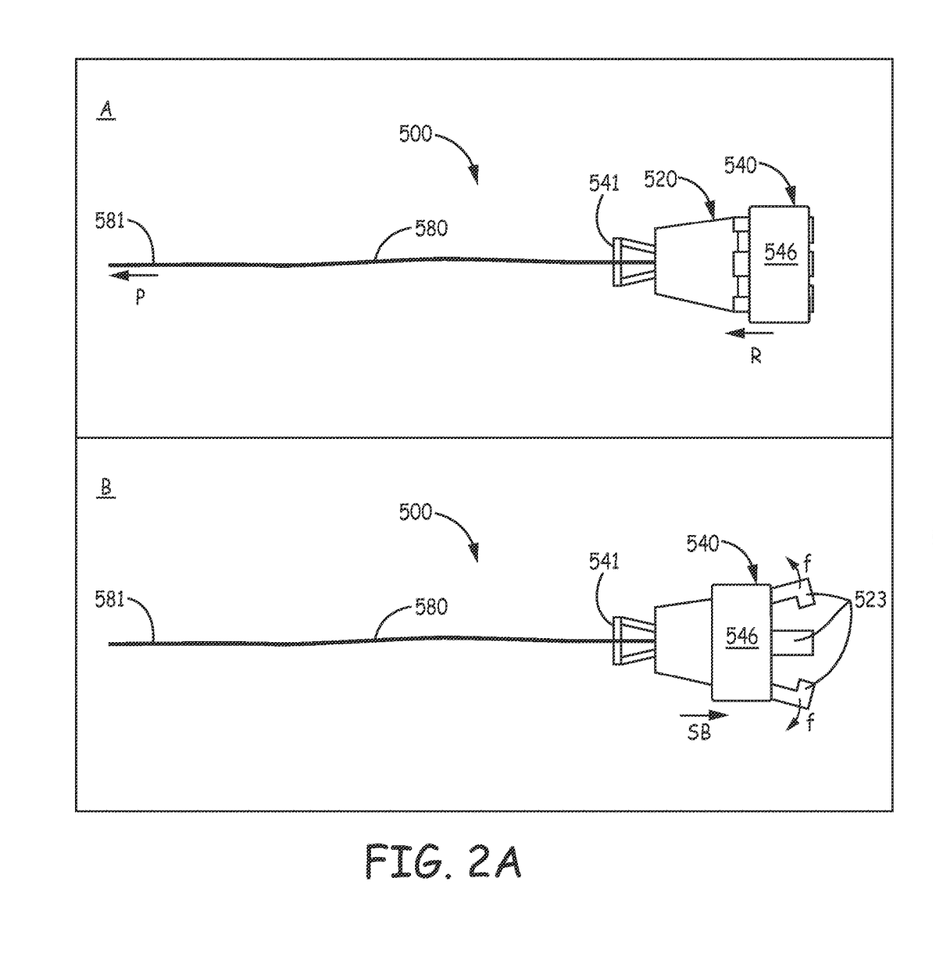
FIG. 2A includes two plan views of a tethering assembly of a first type for a delivery catheter, according to some embodiments.

FIG. 2A includes two plan views of a tethering assembly 500 of a first type for a delivery catheter, according to some embodiments. FIG. 2A illustrates tethering assembly 500 including a collet 520 and a spring-biased holding element 540 that is moveable with respect to collet 520 between a first position A and a second position B. FIG. 2A further illustrates a plurality of elastic fingers 523 forming a distal portion of collet 520, and a collar 546 of holding element 540 that extends around fingers 523 in first position A. Fingers 523 are configured to grip around a proximal end of an implantable medical device, for example, as described below in conjunction with FIG. 4. According to the illustrated embodiment, holding element 540 may be retracted, per arrow R, against the spring bias thereof, to second position B, at which elastic fingers 523 flex outward, per arrows f. Arrow SB indicates the direction of the spring bias to move holding element 540 from second position B back to first position A, when an external force that keeps holding element 540 in second position B is released.

Figure 2B:
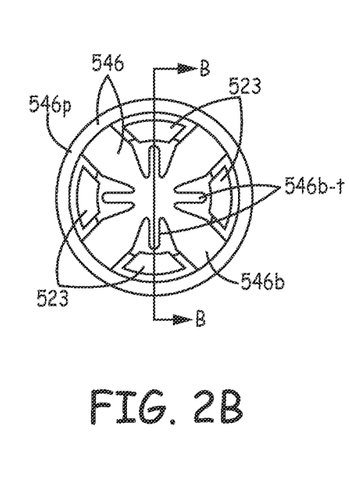
FIG. 2B is an end view of the tethering assembly of FIG. 2A, according to some embodiments.
Figure 2C:
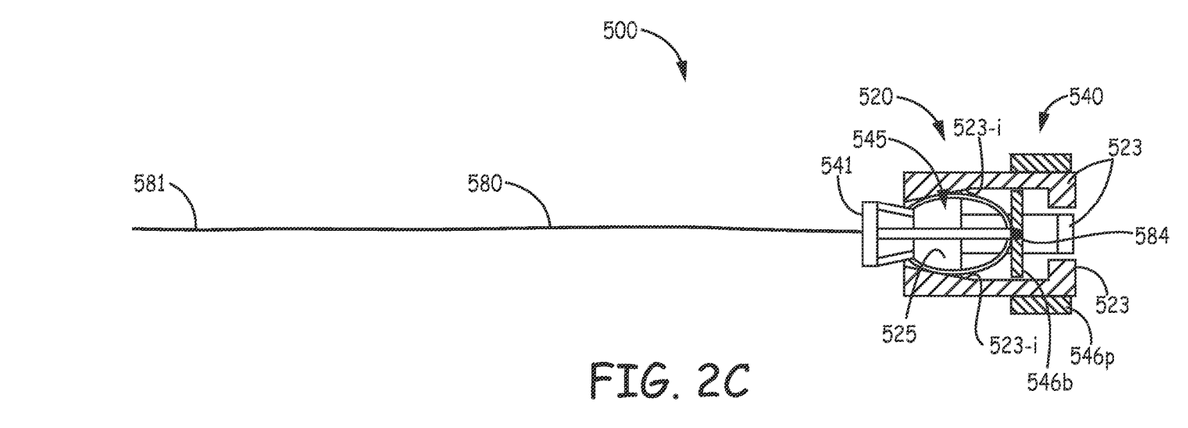
FIG. 2C is a longitudinal cross-section view, per section line B-B of FIG. 2B, according to some embodiments.

FIG. 2B is an end view of tethering assembly 500, according to some embodiments. FIG. 2B illustrates holding element collar 546 including a perimeter portion 546p and a base portion 546b, wherein perimeter portion 546p extends around an outer perimeter of collet elastic fingers 523, and base portion 546b extends between fingers 523. With reference back to FIG. 2A, in conjunction with FIG. 2C, which is a longitudinal cross-section view through section line B-B of FIG. 2B, tethering assembly 500 further includes an elongate tether 580, which has a distal end 584 thereof coupled to collar base portion 546b of spring-biased holding element 540, so that an external pull force P applied to a proximal end 581 of tether 580 may retract holding element 540, per arrow R, against the spring bias thereof, when a backup force is applied to a proximal end 541 of holding element 540. FIG. 2C illustrates holding element 540 including a spring member 545 formed by a plurality of leaf springs extending over a length within an interior portion 525 of collet 520, and, for example, being joined together at proximal end 541 and in proximity to tether distal end 584, and being spaced apart from one another around a perimeter of interior portion 525 in a bulb-like shape. With further reference to FIG. 2B, collar base portion 546b may include tongue features 546b-t, each of which is aligned with a corresponding leaf spring of spring member 545; and FIG. 2C further illustrates collet fingers 523 including inclined inner surfaces 523-i, wherein each inner surface 523-i interfaces with a corresponding tongue feature 546b-t and leaf spring of spring member 545, such that, when holding element 540 is moved proximally to second position B (FIG. 2A), collet fingers 523 are caused to open, or flex outward, per arrows f. According to some preferred embodiments, collet fingers 523 are spring-biased toward a closed, or gripping position, which is secured by holding element 540 in first position A.

Figure 2D:
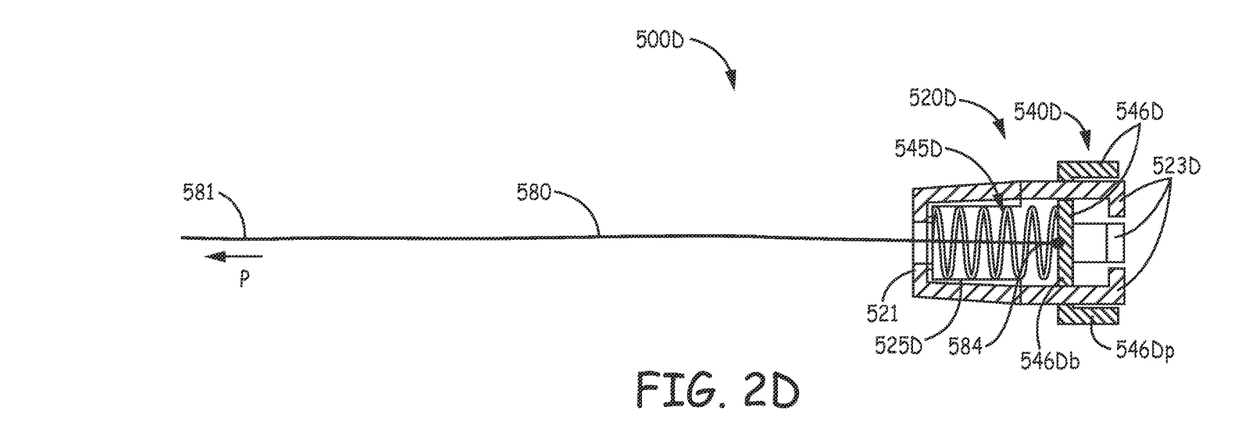
FIG. 2D is longitudinal cross-section view of an alternate embodiment of the first type of tethering assembly.

FIG. 2D is longitudinal cross-section view of a tethering assembly 500D according to an alternate embodiment of the first type. FIG. 2D illustrates a spring-biased holding element 540D of tethering assembly 500D including a collar 546D and a spring member 545D, wherein collar 546D, like collar 546 of holding element 540 of tethering assembly 500, includes a base portion 546Db and a perimeter portion 546Dp, and wherein spring member 545D is in the form of a coil, which is mounted within an interior portion 525D of a collet 520D of tethering assembly 500D. Assembly 500D, like assembly 500, is shown including tether 580, and tether distal end 584 is shown coupled to base portion 546Db of holding element collar 546D. With further reference to FIG. 2D, a proximal end 521 of collet 520D is configured to receive the above-described backup force that allows pull force P, applied through tether 580, to retract holding element 540D proximally from around elastic fingers 523D of collet 520D. According to the illustrated embodiment, collet fingers 523D do not include inclined inner surfaces like those of collet 520 in assembly 500, and, in some embodiments, collet fingers 523D are spring-biased outward, or toward an open position, so that moving spring-biased holding element 540D proximally allows fingers 523D to free flex outward, according to the spring bias thereof. Alternately, collet fingers 523D may be spring-biased to the closed or gripping position, which is secured by spring-biased holding element 540D, so that, when holding element 540D is moved proximally from around fingers 523D, a sufficient force is required either to push the aforementioned device proximal end (FIG. 4) into collet 520D, between fingers 523D, or to pull tethering assembly 500D out of engagement with the device proximal end.

Figure 4:
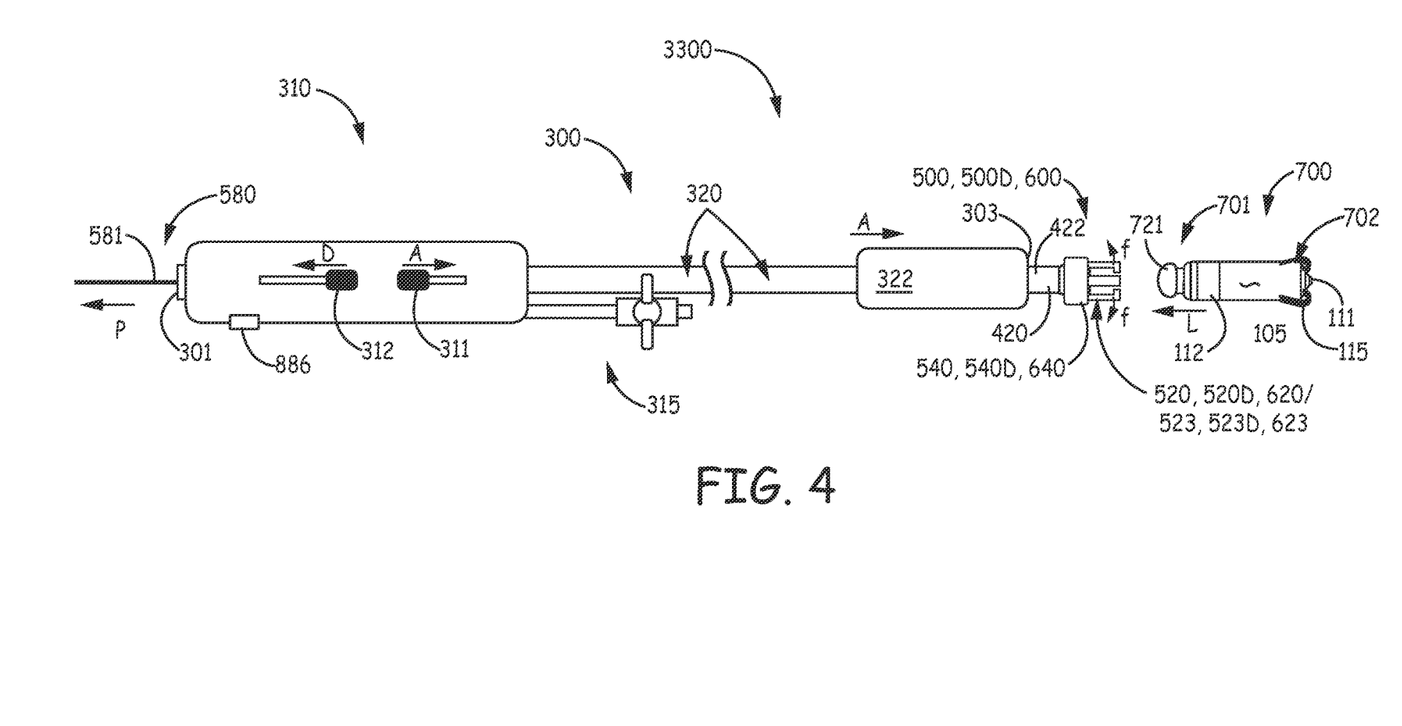
FIG. 4 is a plan view of an interventional medical system, according to some embodiments.
Figure 5A:
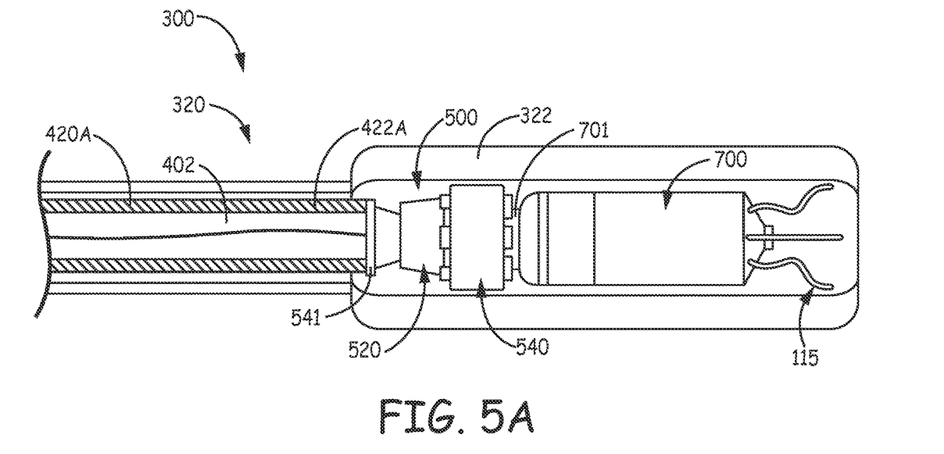
FIGS. 5A-B are longitudinal cross-section views through a distal portion of a delivery catheter of the system of FIG. 4, according to some alternate embodiments, when an implantable medical device is tethered thereto.

With further reference to FIGS. 2A and 2C-D, proximal end 541 of holding element 540 in assembly 500, and proximal end 521 of collet 520D in assembly 500D, are each configured to butt up against a distal end of an elongate tubular member of a delivery catheter, for example, a tubular member 420 of a catheter 300 shown in FIGS. 4 and 5A. Thus, the tubular member 420, when abutting proximal end 541, 521, provides a back-up force for retracting holding element collar 546, 546D against the biasing force of spring member 545, 545D.

According to an exemplary embodiment, tether 580, for example, formed from a polyester fiber having a fluoropolymer coating such as PTFE, has a cross-section and length sized for sliding engagement within a lumen of catheter tubular member 420, and a knot in tether distal end 584 may secure tether 580 to a feature of collar base portion 546b, 546Db. Furthermore, collet 520, 520D may be formed from a suitable medical grade Nitinol, or a relatively rigid plastic, such as nylon, or a combination thereof; and holding element 540, 540D may be formed from a suitable medical grade stainless steel, titanium, MP35N, or nylon, or any appropriate combination thereof.

Figures 3A, 3B:
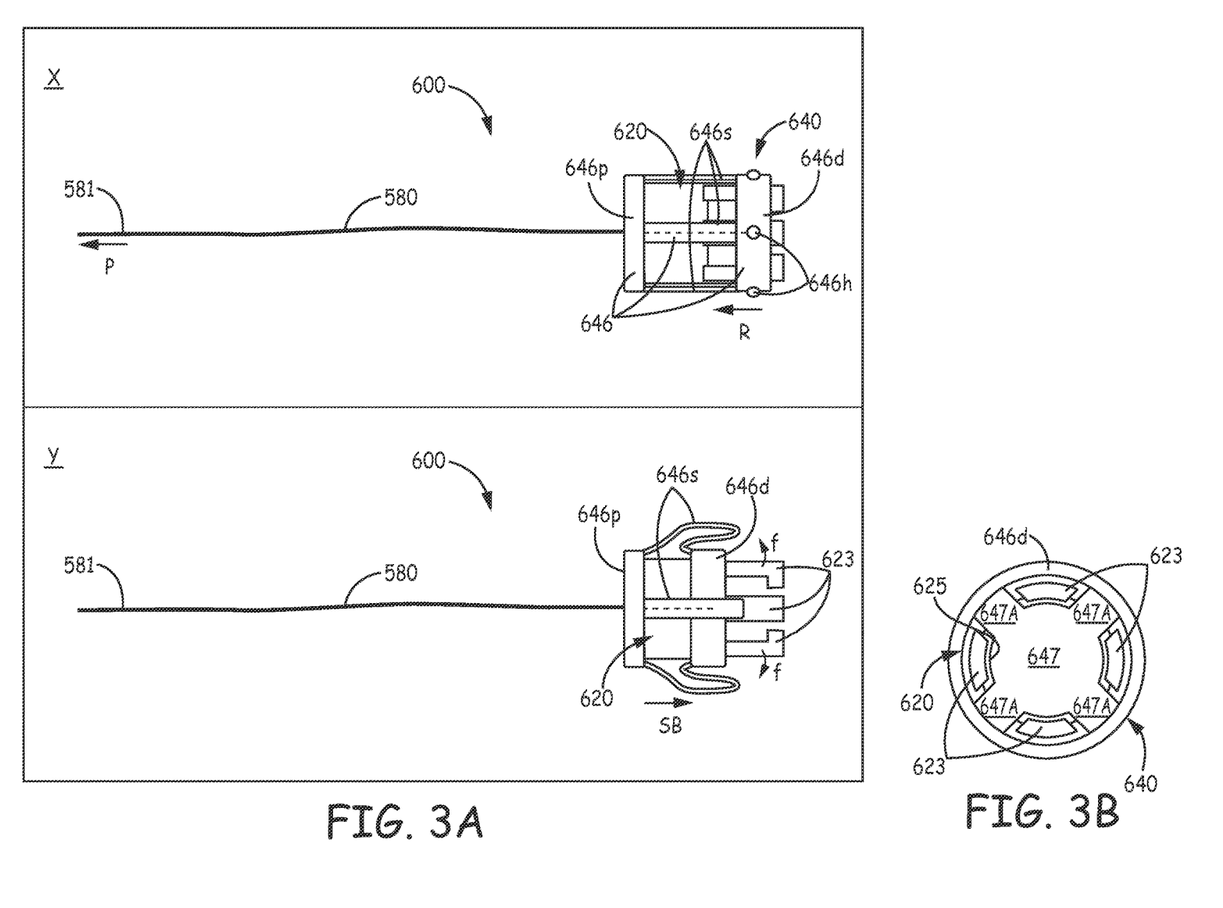
FIG. 3A includes two plan views of a tethering assembly of a second type for a delivery catheter, according to some embodiments.
FIG. 3B is an end view of the tethering assembly of FIG. 3A, according to some embodiments.

FIG. 3A includes two plan views of a tethering assembly 600 of a second type for a delivery catheter, according to some embodiments. Like tethering assembly 500, tethering assembly 600 includes tether 580, a collet 620 and a spring-biased holding element 640 that is moveable with respect to collet 620 between a first position X and a second position Y, for example, by applying external force P to tether 580. Collet 620, like collet 520, may be formed by a suitable medical grade Nitinol, or a relatively rigid plastic, such as nylon, or a combination thereof, wherein a distal portion thereof is formed by elastic fingers 623 that may be spring-biased toward a closed, or gripping position, or spring-biased outward, or toward an open position. In either case, collet fingers 623 are free to flex outward, per arrows f, either by spring-bias or an external force, when holding element 640 is in second position Y. FIG. 3A illustrates an elastic ring 646 of holding element 640 including a distal collar 646d, a proximal base 646p, and a plurality of struts 646s extending therebetween. According to an exemplary embodiment, elastic ring 646 is formed from medical grade Nitinol, for example, being cut from a Nitinol tube according to methods known to those skilled in the art. With reference to FIG. 3B, which is an end view of tethering assembly 600, holding element 640 further includes a plate 647 that extends within an interior portion 625 of collet 620, and to which the distal end of tether 580, which also extends within interior portion 625 (shown with dashed lines in FIG. 3A), is coupled, for example, via a knot thereof secured to a feature of plate 647 (not shown). Plate 647 may be formed from a suitable medical grade stainless steel, titanium, MP35N, or nylon, or any appropriate combination thereof, and FIG. 3B further illustrates plate 647 of holding element 640 including a plurality of arms 647A that are spaced apart from one another around a perimeter of plate 647, wherein each arm 647A extends between adjacent elastic fingers 623 of collet 620, being coupled to distal collar 646d of elastic ring 646, for example, by an interlocking fit, for example, through holes 646h of distal collar 646d shown in FIG. 3A, which may be secured by welding or crimping in some embodiments.

Figure 5B:
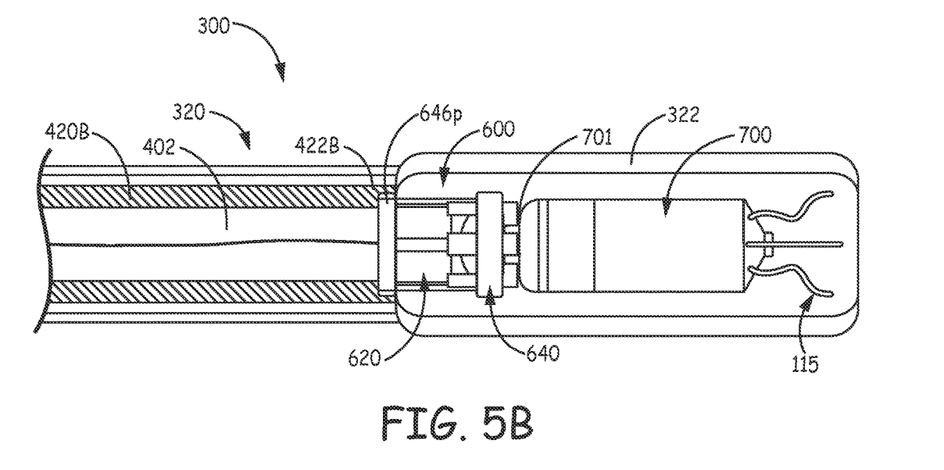

According to the illustrated embodiment, holding element plate 647 translates the pull force P from tether 580 to holding element distal collar 646d, to retract distal collar 646d, per arrow R, against the spring bias of struts 646s, for example, when holding element proximal base 646p butts up against a distal end of a tubular member of a delivery catheter, for example, tubular member 420 of catheter 300 (FIGS. 4 and 5B). With further reference to FIG. 3A, holding element distal collar 646d extends around collet fingers 623, when holding element 640 is in first position X, and retracting holding element 640 to second position Y, per arrow R, causes struts 646s to flex and bend so that collar 646d is drawn proximally into an interior portion of elastic ring 646. Arrow SB indicates the direction of the spring bias to move holding element 640 from second position Y back to first position X, when the external force that keeps holding element 640 in second position Y is released.

FIG. 4 is a plan view of an interventional medical system 3300, which may incorporate any of the above-described embodiments of tethering assemblies 500, 500D, 600 of either type. FIG. 4 illustrates system 3300 including an implantable medical device 700 and a delivery catheter 300 for deploying device 700 at an implant site, for example, within a patient's right ventricle RV (FIG. 1). Like device 100, described above in conjunction with FIG. 1, device 700 includes an electronic controller and associated power source (not shown) contained in hermetically sealed housing 105, wherein electrode 111, being mounted to housing 105 at a distal end 702 of device 700, is electrically coupled to the controller, for example, by any suitable type of hermetically sealed feedthrough assembly known to those skilled in the art. Also like device 100, a portion of the insulation layer overlaying housing 105 of device 700 may be removed to form another electrode 112, for example, to provide bipolar pacing and sensing in conjunction with electrode 111. According to the illustrated embodiment, a proximal end 701 of device 700 includes a knob-like member 721, which collet fingers 523, 523D, 623 of any of the above-described tethering assemblies 500, 500D, 600 are configured to grip, when device 700 is inserted, per arrow L, into the distal portion of collet 520, 520D, 620, as will be described in greater detail below.

Figure 6:
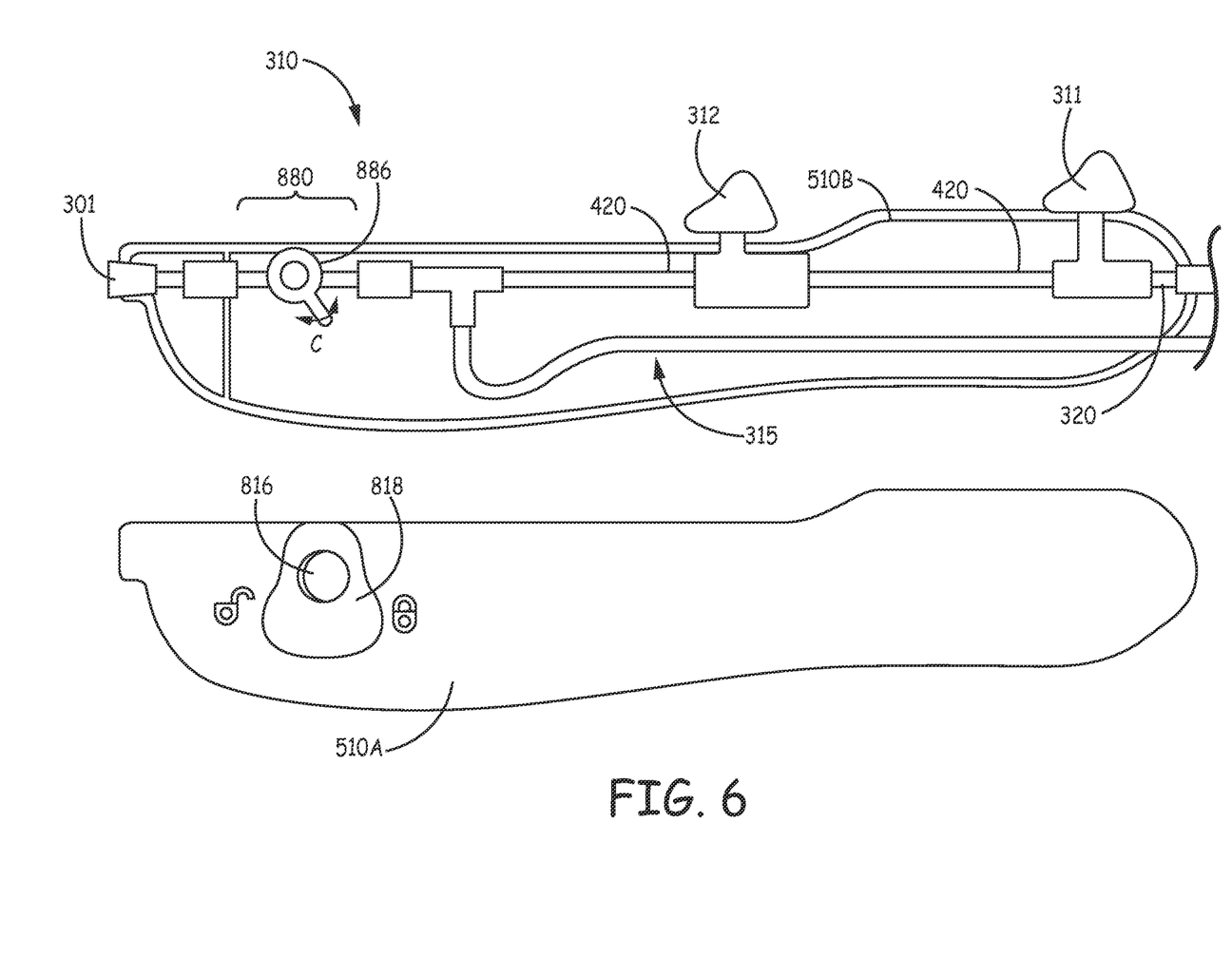
FIG. 6 is a plan view of an interior of a handle of the delivery catheter, according to some embodiments.

FIG. 4 further illustrates catheter 300 including a handle 310, an outer shaft 320, elongate tubular member 420, around which shaft 320 is slideably engaged, and a flushing assembly 315 coupled to handle 310 and in fluid communication with a lumen 402 of tubular member 420 (FIGS. 5A-B and 6). According to the illustrated embodiment, shaft 320 is coupled to a control member 311 of handle 310, which is operable to retract and advance shaft 320 relative to tubular member 420. FIG. 4 illustrates shaft 320 retracted relative to tubular member 420, so that the distal end of tubular member 420 extends from a distal opening 303 of the lumen of shaft 320, distal opening 303 being defined by a distal-most portion 322 of shaft 320, which is sized to contain device 700 therein, for example, as shown in FIGS. 5A-B. According to some embodiments, outer shaft 320 may be constructed in a similar fashion to a deployment tube of a tool described in co-pending and commonly assigned U.S. Patent Application US 2015/0094668, Ser. No. 14/039,937.

FIG. 4 further illustrates tethering assembly 500, 500D, 600 abutting the distal end of tubular member 420, having been coupled thereto by inserting tether 580 through lumen 402 of tubular member 420 (FIGS. 5A-B) so that tether proximal end 581 extends out through a proximal port opening 301 of handle 310, at a proximal end of catheter 300. According to some methods of the present invention, device 700 is tethered to catheter 300, after coupling tethering assembly 500, 600 to tubular member 420, first by applying the external pull force P to tether proximal end 581, which moves holding element 520, 620 proximally (e.g., to second position B, Y—FIGS. 2A, 3A), thereby allowing and/or causing the opening, or the flexing outward of the fingers 523, 523D, 623 of collet 520, 520D, 620, per arrows f, and then by inserting knob-like member 721 of device proximal end 701, per arrow L, between collet fingers 523, 523D, 623, after which the pull force P is released thereby allowing holding element 540, 540D, 640 to move distally (e.g., to first position A, X—FIGS. 2A, 3A), according to the spring bias thereof, so that the grip of fingers 523, 523D, 623 around device proximal end 701 is secured. By some methods, after applying pull force P to retract holding element 540, 540D, 640, tether 580 may be locked in place within handle 310, for example, by a stopcock-type valve member 880 thereof that is described in greater detail below (FIG. 6), while device 700 is inserted into collet 520, 520D, 620, after which the lock on tether 580 is released, thereby allowing holding element 540, 540D, 640 to move distally according to the spring bias thereof. According to some alternate methods, device proximal end 701 may be inserted and secured within collet 520, 520D, 620 before tethering assembly 500, 500D, 600 is coupled to tubular member 420.

With further reference to FIG. 4, according to some methods, once tethering assembly 500, 500D, 600 is coupled to catheter 300, and device 700 is coupled to tethering assembly 500, 500D, 600, outer shaft 320 is advanced relative to tubular member 420, for example, by moving control member 311 per arrow A, until shaft distal-most portion 322 encloses the secured device 700, for example, as illustrated in FIGS. 5A-B, wherein FIG. 5A shows tethering assembly 500 and FIG. 5B shows tethering assembly 600. With reference to FIGS. 5A-B, advancing outer shaft 320 over device 700 moves a plurality of elastic fixation fingers of fixation member 115 from a relaxed condition (FIG. 4) to an extended condition. Fixation member 115 may be cut from Nitinol tubing, according to methods known in the art, and fixation member 115 may be mounted to device housing 105 in a manner similar to that described for a fixation component in co-pending and commonly assigned United States Patent Application 2012/0172690. The super-elastic nature of Nitinol allows the fingers of fixation member 115 to elastically deform between the relaxed and extended conditions.

According to some methods, after device 700 is secured in the grip of tethering assembly 500, 600, for example, prior to advancing outer shaft 320 per arrow A (FIGS. 4, 5A-B), the operator may lock, or clamp tether 580 in place within handle 310, for example, by the aforementioned valve member 880, which can be seen in FIG. 6. FIG. 6 is a plan view of an internal configuration of handle 310 wherein a first portion of an outer surface, or shell 510A of handle 310 is removed to see an arrangement of components within a second portion of the shell 510B. FIG. 6 shows valve member 880 integrated into a conduit of handle 310, through which tether 580 extends between lumen 402 of tubular member 420 and proximal port opening 301 of handle 310. According to the illustrated embodiment, valve member 880 is in the form of a stopcock-type valve, known to those skilled in the art, that includes a lever 886, wherein lever 886 extends through an aperture 816 formed through a recessed surface 818 of first portion of shell 510A, when shell portions 510A, 510B are secured together, so that an operator has access thereto for locking and unlocking tether 580 by rotating lever 886 per arrow C. Having tether 580 locked in place while the operator maneuvers delivery catheter 300, for example, within a patient's venous system to an implant site, may be desirable to prevent an inadvertent pull force P on tether proximal end 581 that could retract tethering assembly holding element 540, 640.

When device proximal end 701 is secured within tethering assembly collet 520, 620, and distal-most portion 322 of outer shaft 320 contains the tethered and secured device 700, for example, as shown in FIGS. 5A-B, the operator may advance delivery catheter 300 into a body of a patient, for example, the patient's venous system, and maneuver distal-most portion 322 into proximity with an implant site, for example, in the right ventricle RV (FIG. 1). With reference back to FIG. 4, tubular member 420 may be deflectable to facilitate the maneuvering of catheter 300, for example, having a pull wire integrated therewith (not shown), wherein a distal end of the pull wire is anchored in proximity to a distal end 422 of tubular member 420, and a proximal end of the pull wire is coupled to another control member 312 of handle 310, which when moved per arrow D deflects tubular member 420 together with outer shaft 320 to better orient distal-most portion 322 toward the implant site. Tubular member 420 may be extruded polyether block amide, polyurethane, or silicone rubber, or a composite thereof, and may include an overlay (not shown), for example, formed of braid-reinforced polyether block amide. With further reference to FIGS. 5A-B, a configuration of the distal end of tubular member 420 may depend upon which type of tethering assembly is employed by catheter 300. FIG. 5A illustrates tubular member distal end 422A abutting holding element proximal end 541; and FIG. 5A illustrates tubular member distal end 422B abutting holding element 640 such that elastic ring proximal base 646p is fitted to distal end 422B, for example, in a recess thereof. In either case, the abutting engagement provides the necessary backup force to retract holding element 540, 640, for example, as described below.

Figure 7A:
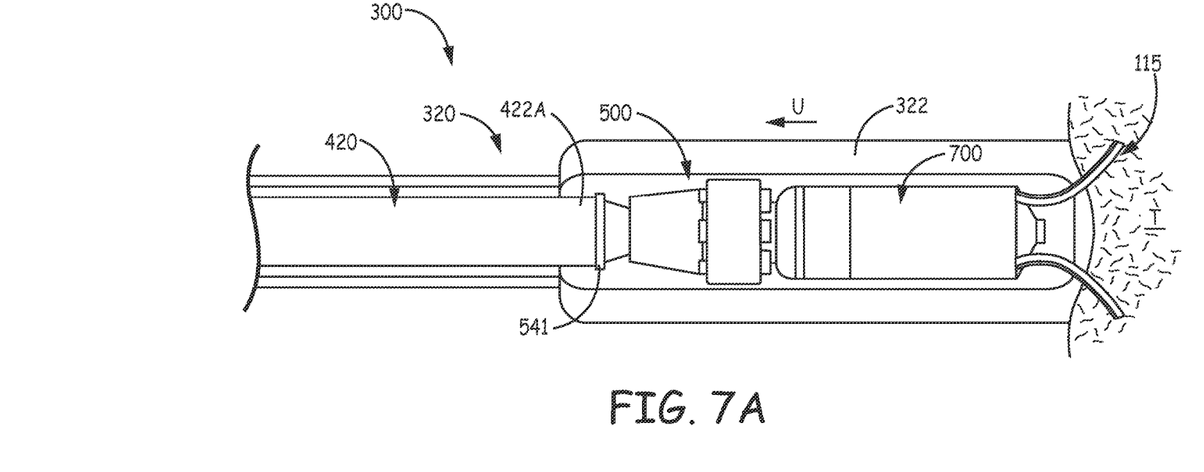
FIGS. 7A-C are schematics pertaining to methods for deploying the device from the delivery catheter.
Figure 7B:
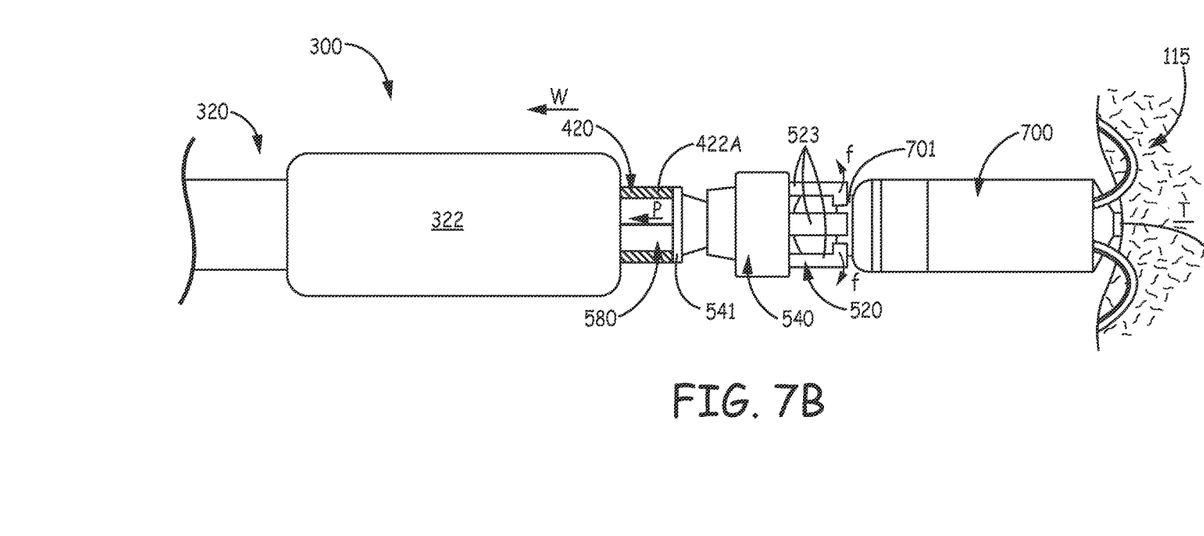
Figure 7C:
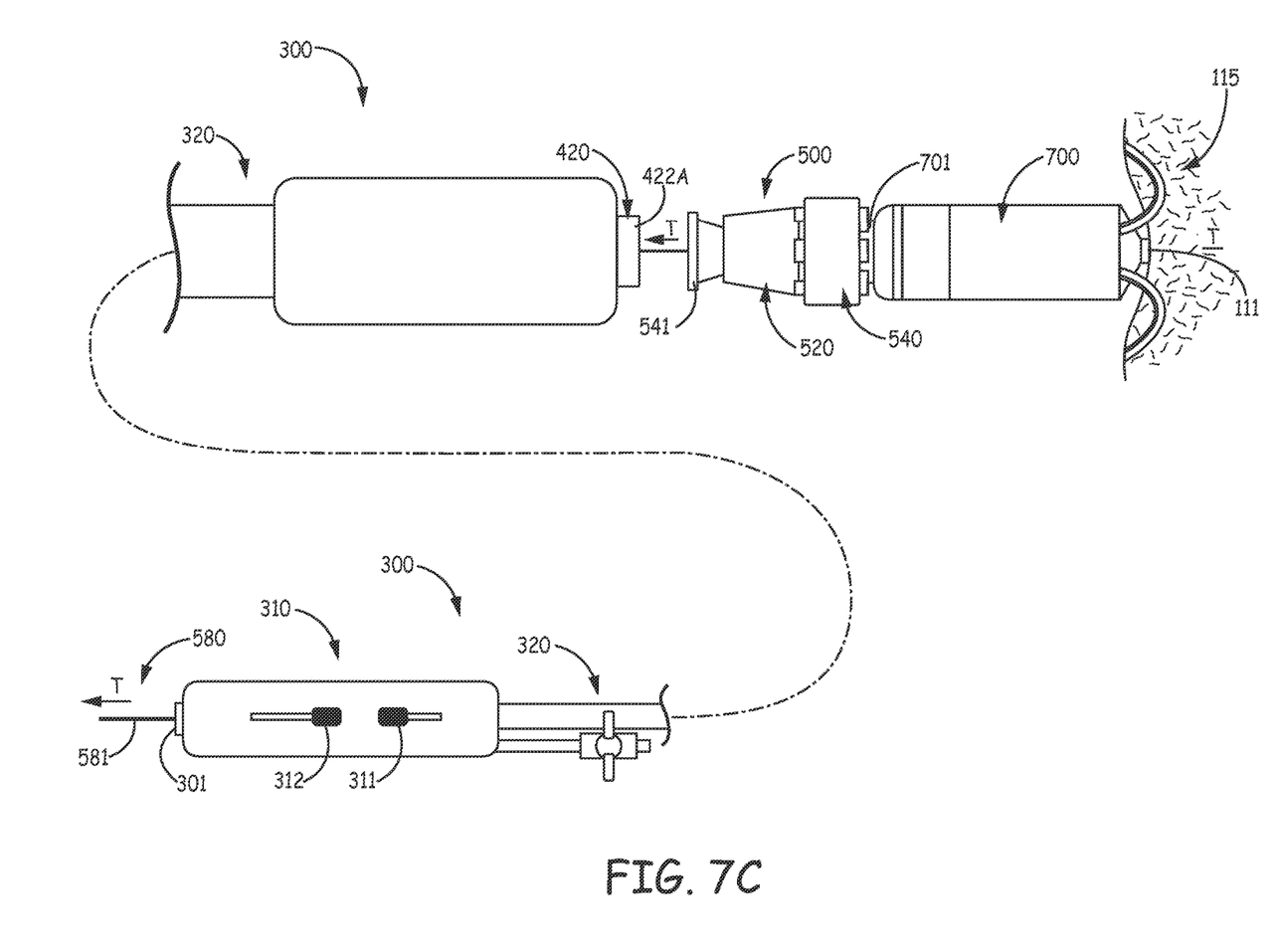

FIGS. 7A-C are schematics that show fixation fingers of device fixation member 115 engaging with tissue T at an implant site when the operator retracts catheter outer shaft 320, per arrow U, relative to tubular member 420 and secured device 700, for example, via control member 311 (FIG. 4). Note that FIGS. 7A-C illustrate tethering assembly 500, although the ensuing description makes reference to tethering assemblies 500D and 600 as well, since the described methods are somewhat the same for both. Once fixation member 115 is engaged with the tissue T, the operator may retract spring biased holding element 540, 640 of tethering assembly 500, 600 to second position B, Y (shown in FIGS. 2A, 3A), for example, applying the pull force P to tether proximal end 581 (FIG. 4), after unlocking tether 580, if previously locked in place in handle 310, as described above. With reference to FIG. 7B the pull force P is shown being backed up by the abutting distal end 422A of tubular member 420, so that holding element 540 is retracted against the spring bias thereof. Once the operator has retracted holding element 540, collet fingers 523 flex outward, per arrows f, as described above, so that the operator may withdraw an entirety of catheter 300, per arrow W, proximally away from implanted device 700. Alternately, for example, in the case of tethering assembly 500D or 600, collet fingers 523D, 623 are free to flex outward when holding element 540D or 640 is retracted, either according to a spring-bias of the collet fingers, in some embodiments, or in response to the force of withdrawing catheter 300 away from the implanted device 700.

According to some methods, the operator will test the fixation of engaged device fixation member 115 by withdrawing an entirety of catheter 300 proximally from the implanted device 700 before retracting holding element 540, 540D, 640 of tethering assembly 500, 500D, 600, such that tubular member distal end 422A, 422B no longer abuts tethering assembly 500, 500D, 600, for example, as illustrated in FIG. 7C for assembly 500. FIG. 7C shows a tug force T applied to tether 580, when tubular member 420 is retracted relative to holding element proximal end 541, so that tug force T, without the backup from tubular member distal end 422A, will be transferred through tethering assembly 500, with holding element 540 securing the grip of collet 520 around device proximal end 701, to device 700. If fixation of device 700 at the implant site is secure, the operator can move catheter 300 distally over tether 580 so that tubular member 420 one again abuts holding element proximal end 541 to provide the backup force for retracting spring-biased holding element 540 as described above.

In the foregoing detailed description, the invention has been described with reference to specific embodiments. However, it may be appreciated that various modifications and changes can be made without departing from the scope of the invention as set forth in the appended claims.

The invention claimed is:

1. An interventional medical system comprising an implantable medical device and a delivery catheter for deploying the device at an implant site, the device comprising a housing, an electrode mounted to the housing, and a fixation member mounted to a distal end of the housing, wherein a proximal end of the device comprises a knob-like member, and the catheter comprising:
   an elongate tubular member extending from a proximal end thereof to a distal end thereof and being moveable between a first position of the tubular member and a second position of the tubular member, the tubular member including a lumen that extends along a length thereof, from a proximal opening, at the proximal end, to a distal opening, at the distal end; and
   a tethering assembly coupled to the tubular member, the tethering assembly comprising a tether, a collet, and a spring-biased holding element, the tether extending from a proximal end thereof to a distal end thereof and within the lumen of the tubular member, the distal end of the tether being coupled to the spring-biased holding element, the collet being located in proximity to the distal end of the tubular member and including a plurality of elastic fingers configured to grip around the knob-like member at the proximal end of the device, the spring-biased holding element interfacing with the collet and being movable between a first position of the spring-biased holding element and a second position of the spring-biased holding element,
   wherein when the tubular member is in the first position of the tubular member, the tubular member does not abut the tethering assembly, and wherein when the tubular member is in the second position of the tubular member, the tubular member abuts the tethering assembly,
   wherein the spring-biased holding element is spring biased to the first position of the spring-biased holding element, at which the holding element prevents an opening of the fingers of the collet, and
   wherein the spring-biased holding element is moved against the spring bias thereof to the second position of the spring-biased holding element to trigger the holding element to open the fingers of the collet, the holding element being moved to the second position of the spring-biased holding element by applying a pull force to the tether when the tubular member is held abutting the tethering assembly in the second position of the tubular member.

2. The system of claim 1, wherein the spring-biased holding element of the tethering assembly comprises a collar and a spring member, the tether being coupled to the collar, the collar extending around the collet and between the fingers thereof, and the spring member being mounted within an interior portion of the collet.

3. The system of claim 2, wherein the spring member of the spring-biased holding element comprises a coiled spring.

4. The system of claim 2, wherein the spring member of the spring-biased holding element comprises a plurality of leaf springs.

5. The system of claim 4, wherein each collet finger of the tethering assembly includes an inclined inner surface interfacing with the spring-biased holding element, such that the collect fingers are caused to open by the movement of the holding element to the second position of the spring-biased holding element.

6. The system of claim 1, wherein the spring-biased holding element of the tethering assembly comprises an elastic ring and a plate, the tether being coupled to the plate, the elastic ring extending around the collet and including a distal collar and a proximal base, the base being fitted to the distal end of the tubular member and surrounding the distal opening of the lumen thereof, the plate extending within an interior portion of the collet and including a plurality of arms spaced apart from one another around a perimeter of the plate, each arm extending between adjacent fingers of the collet, and each arm being coupled to the distal collar of the elastic ring.

7. The system of claim 6, wherein, when the holding element is moved to the second position of the spring-biased holding element, the distal collar of the elastic ring of the holding element is drawn proximally into an interior portion of the elastic ring.

8. The system of claim 1, wherein the catheter further comprises an outer shaft slidably engaged around the tubular member, the outer shaft including a distal-most portion sized to contain the device therein, when the device is gripped by the collet of the tethering assembly.

9. The system of claim 1, wherein the device comprises an electronic controller and an associated power source, the housing being hermetically sealed and containing the controller and power source, and the electrode electrically coupled to the controller.

10. The system of claim 1, wherein the spring-biased holding element remains in the first position of the spring-biased holding element when the pull force is applied to the tether when the tubular member is in the first position of the tubular member.

11. A tethering assembly for a delivery catheter, the catheter for deploying an implantable medical device at an implant site, the device comprising a housing, an electrode mounted to the housing, and a fixation member mounted to a distal end of the housing, wherein a proximal end of the device comprises a knob-like member, the tethering assembly being configured for coupling to an elongate tubular member of the catheter, the tubular member being moveable between a first position of the tubular member and a second position of the tubular member and the tethering assembly comprising:
   a collet including a plurality of elastic fingers configured to grip around the knob-like member of the proximal end of the device; and
   a spring-biased holding element interfacing with the collet and being movable between a first position of the spring-biased holding element and a second position of the spring-biased holding element; and
   an elongate tether extending from a proximal end thereof to a distal end thereof, the distal end being coupled to the spring-biased holding element,
   wherein when the tubular member is in the first position of the tubular member, the tubular member does not abut the tethering assembly, and wherein when the tubular member is in the second position of the tubular member, the tubular member abuts the tethering assembly,
   wherein the spring-biased holding element is spring biased to the first position of the spring-biased holding element, at which the holding element prevents an opening of the fingers of the collet, and
   wherein the spring-biased holding element is moved against the spring bias thereof to the second position of the spring-biased holding element to trigger the holding element to open the fingers of the collet, the holding element being moved to the second position of the spring-biased holding element by applying a pull force to the tether when the tubular member is held abutting the tethering assembly in the second position of the tubular member.

12. The tethering assembly of claim 11, wherein the spring-biased holding element comprises a collar and a spring member, the tether being coupled to the collar, the collar extending around the collet and between the fingers thereof, and the spring member being mounted within an interior portion of the collet.

13. The tethering assembly of claim 12, wherein the spring member of the spring-biased holding element comprises a coiled spring.

14. The tethering assembly of claim 12, wherein the spring member of the spring-biased holding element comprises a plurality of leaf springs.

15. The tethering assembly of claim 14, wherein each collet finger includes an inclined inner surface interfacing with the spring-biased holding element, such that the collect fingers are caused to open by the movement of the holding element to the second position of the spring-biased holding element.

16. The tethering assembly of claim 11, wherein the spring-biased holding element comprises a plate and an elastic ring, the tether being coupled to the plate, the elastic ring extending around the collet and including a distal collar and a proximal base, the base being configured for fitting to a distal end of the tubular member, the plate extending within an interior portion of the collet and including a plurality of arms spaced apart from one another around a perimeter of the plate, each arm extending between adjacent fingers of the collet, and each arm being coupled to the distal collar of the elastic ring.

17. The tethering assembly of claim 16, wherein, when the holding element is moved to the second position of the spring-biased holding element, the distal collar of the elastic ring of the holding element is drawn proximally into an interior portion of the elastic ring.

18. The system of claim 11, wherein the spring-biased holding element remains in the first position of the spring-biased holding element when the pull force is applied to the tether when the tubular member is in the first position of the tubular member.

* * * * *